(12) United States Patent
Green et al.

(10) Patent No.: US 8,765,356 B2
(45) Date of Patent: Jul. 1, 2014

(54) CALIXARENE COMPOUND AND PHOTORESIST COMPOSITION COMPRISING SAME

(71) Applicant: Rohm and Haas Electronic Materials LLC, Marlborough, MA (US)

(72) Inventors: D. Patrick Green, Midland, MI (US); Vipul Jain, Westborough, MA (US); Brad C. Bailey, Midland, MI (US)

(73) Assignees: Dow Global Technologies LLC, Midland, MI (US); Rohm and Haas Electronics Materials LLC, Marlborough, MA (US)

(*) Notice: Subject to any disclaimer, the term of this patent is extended or adjusted under 35 U.S.C. 154(b) by 0 days.

(21) Appl. No.: 13/624,597

(22) Filed: Sep. 21, 2012

(65) Prior Publication Data
US 2013/0157195 A1    Jun. 20, 2013

Related U.S. Application Data

(60) Provisional application No. 61/538,672, filed on Sep. 23, 2011.

(51) Int. Cl.
*G03F 7/004* (2006.01)
*G03F 7/039* (2006.01)
*C07C 41/00* (2006.01)

(52) U.S. Cl.
USPC .................. 430/270.1; 430/326; 562/632

(58) Field of Classification Search
USPC ............... 430/270.1, 326; 562/630, 631, 632
See application file for complete search history.

(56) References Cited

U.S. PATENT DOCUMENTS

| | | | |
|---|---|---|---|
| 6,093,517 | A | 7/2000 | Ito et al. |
| 7,037,638 | B1 | 5/2006 | Afzali-Ardakani et al. |
| 7,514,197 | B2 | 4/2009 | Ochiai et al. |
| 7,642,145 | B2 | 1/2010 | Fukuda et al. |
| 7,659,047 | B2 | 2/2010 | Kojima et al. |
| 7,705,189 | B2 | 4/2010 | Nishikubo et al. |
| 2005/0026077 | A1* | 2/2005 | Gronbeck et al. ......... 430/270.1 |
| 2005/0271971 | A1 | 12/2005 | Ueda et al. |
| 2007/0122734 | A1 | 5/2007 | Roberts et al. |
| 2007/0224540 | A1 | 9/2007 | Kamimura et al. |
| 2010/0239980 | A1 | 9/2010 | Okuyama et al. |
| 2011/0020756 | A1 | 1/2011 | Bozano et al. |
| 2012/0107749 | A1 | 5/2012 | Tono et al. |

FOREIGN PATENT DOCUMENTS

| | | |
|---|---|---|
| EP | 1345080 A2 | 9/2003 |
| EP | 1767991 A2 | 3/2007 |
| EP | 1830228 A1 | 9/2007 |
| EP | 1906241 A1 | 4/2008 |
| EP | 1906248 A1 | 4/2008 |
| EP | 2080750 A1 | 7/2009 |
| JP | 2008116677 A | 5/2008 |
| JP | 2009173625 A | 8/2009 |
| WO | 2004036315 A1 | 4/2004 |
| WO | 2005097725 A1 | 10/2005 |
| WO | 2006129574 A1 | 12/2006 |
| WO | 2009075307 A1 | 6/2009 |
| WO | 2009075308 A1 | 6/2009 |
| WO | 2009119784 A1 | 10/2009 |
| WO | 2009143357 A2 | 11/2009 |
| WO | 2010026973 A1 | 3/2010 |
| WO | 2010067627 A1 | 6/2010 |

OTHER PUBLICATIONS

International Publication No. 2004036315 A1; Publication Date: Apr. 29, 2004; Abstract Only, 2 pages.
International Publication No. 2005097725 A1; Publication Date: Oct. 20, 2005; Abstract Only, 2 pages.
International Publication No. 2006129574 A1; Publication Date: Dec. 7, 2006; Abstract Only, 2 pages.
Japanese Patent No. 2008116677 A; Publication Date: May 22, 2008; Abstract Only, 1 page.
International Publication No. 2009075307 A1; Publication Date: Jun. 18, 2009; Abstract Only, 2 pages.
International Publication No. 2009075308 A1; Publication Date: Jun. 18, 2009; Abstract Only, 2 pages.
International Publication No. 2009119784 A1; Publication Date: Oct. 1, 2009; Abstract Only, 2 pages.
Japanese Patent No. 2009173625 A; Publication Date: Aug. 6, 2009; Abstract Only, 2 pages.
International Publication No. 2010067627 A1; Publication Date: Jun. 17, 2010; Abstract Only, 1 page.
CN 1938259 A; English Abstract; Date of Publication Mar. 28, 2007; 1 page.

* cited by examiner

*Primary Examiner* — Anca Eoff
(74) *Attorney, Agent, or Firm* — Cantor Colburn LLP

(57) ABSTRACT

A molecular glass compound includes (A) a tetrameric reaction product of a specific aromatic compound having at least one hydroxy group, and a specific polycyclic or fused polycyclic aromatic aldehyde; and (B) an acid-removable protecting group as an adduct with the hydroxy group of the aromatic compound and/or a hydroxy group of the polycyclic or fused polycyclic aromatic aldehyde. A photoresist composition including the molecular glass compound, and a coated substrate including a layer of the photoresist composition are also disclosed.

9 Claims, No Drawings

CALIXARENE COMPOUND AND PHOTORESIST COMPOSITION COMPRISING SAME

CROSS-REFERENCE TO RELATED APPLICATION

This application is a nonprovisional filing of provisional application 61/538,672, filed Sep. 23, 2011, the content of which is incorporated herein by reference in its entirety.

BACKGROUND

Design rules for advanced generation microlithography (i.e., beyond 193 nm immersion lithography and into next generation optics such as e-beam, X-ray, and extreme ultraviolet (EUV) lithography operating at a very short wavelength of 13.4 nm) are trending toward smaller and smaller dimensions, for example, 30 nm and below. In general, depth of focus (DOF) necessarily decreases with higher resolution due to the higher numerical aperture (NA) and therefore resist thickness also decreases to commensurate the smaller and smaller feature sizes. With narrower linewidths and thinner resist films, consistency issues such as line edge roughness (LER) and resolution take on increasing significance limiting the performance and usefulness of photoresists. These phenomena are of interest in the fabrication of semiconductor devices; for example, excessive LER can lead to poor etch and lack of linewidth control in, for example, transistor and gate architecture, potentially causing short circuits and signal delay. Since the radius of gyration of polymeric materials generally used to prepare EUV photoresists is essentially larger than the LER requirement (i.e., less than 3 nm), small, discrete and well defined molecules which when cast form amorphous films, and commonly known as molecular glasses, have been considered as possible candidates for developing EUV photoresist platforms.

Molecular glasses have been used in negative and positive tone resists. U.S. Patent Application Publication No. 2010/0047709 A1 describes a low outgassing resist based on calix[4]arenes prepared from resorcinol or pyrogallol and a substituted aldehyde having, for example, a pendant phenyl or cyclohexyl group, with dissolution control groups attached to the hydroxy groups of the resorcinol/pyrogallol. However, there remains a need for calix[4]arene based photoresists which have improved resolution to meet the stringent requirements for photoresists having desirably high resolution and low LER, and with further improvement in processing stability.

STATEMENT OF INVENTION

One or more of the above and other deficiencies of the prior art may be overcome by a molecular glass compound in accordance with the invention, comprising a tetrameric reaction product of an aromatic compound of formula (I):

wherein $R^1$ is H, F, $C_{1-20}$ alkyl, $C_{1-20}$ haloalkyl, $C_{6-20}$ aryl, $C_{6-20}$ haloaryl, $C_{7-20}$ aralkyl, or $C_{7-20}$ haloaralkyl, $R^2$ is H, $C_{1-20}$ alkyl, $C_{1-20}$ haloalkyl, x is 6-y and y is 2 or 3, at least one $OR^2$ group is a hydroxy group, and at least two $OR^2$ groups are meta to one another, and a polycyclic or fused polycyclic aromatic aldehyde of formula (II):

wherein $Ar^1$ is a substituted, halosubstituted or unsubstituted $C_{4-20}$ heterocyclic aromatic-containing moiety, or a substituted, halosubstituted or unsubstituted $C_{8-20}$ fused polycyclic aromatic moiety; and an acid-removable protecting group as an adduct with the hydroxy group of the aromatic compound, a hydroxy group of the polycyclic or fused polycyclic aromatic aldehyde, or a combination comprising at least one of the foregoing.

A photoresist, comprises the molecular glass compound, a solvent, and a photoacid generator.

A coated substrate comprises (a) a substrate having one or more layers to be patterned on a surface thereof; and (b) a layer of a photoresist composition over the one or more layers to be patterned.

A method of forming a patterned substrate comprises exposing the coated substrate to activating radiation.

DETAILED DESCRIPTION

Disclosed herein are novel molecular glass compounds having improved glass transition temperatures, and that are based on novel calix[4]arenes prepared from the condensation of hydroxy and/or alkoxy containing aromatic compounds and fused-ring aromatic or heteroaromatic aldehydes. Some or all of the hydroxy groups are reacted with acid cleavable protecting groups and/or non-cleavable pendant groups, to form an adduct which can exhibit alkali-solubility dissolution rate contrast when the acid cleavable groups are removed, or where the adduct is cross-linked. As used herein, "adduct" refers to the addition or condensation product of the acid cleavable protecting groups and/or non-cleavable pendant groups with an aromatic hydroxy group of the calix[4]arene unless otherwise specified.

Calix[4]arenes are discrete cyclic tetrameric compounds having an alternating structure derived from the reaction of a phenolic compound with an aldehyde. The core structure is preferably bowl-shaped tetrameric calix[4]arene formed from aromatic compounds having hydroxy groups and aldehydes preferably also having hydroxy groups. Calix[4]arenes exist in four different conformers: cis-cis-cis, cis-trans-cis, cis-cis-trans, and trans-trans-trans. Typically, the thermodynamically most favored conformer is the cis-cis-cis in which all four arene rings are flipped in the same direction such that the calix[4]arene molecule possesses a C4 symmetry axis, in contrast to the trans-trans-trans isomer which possesses a C2 symmetry axis. When prepared using hydroxyaromatic compounds such as resorcinol (1,3-dihydroxy benzene) for example, the hydroxy groups effectively lock the conformation by geometrically-favored hydrogen-bonding interactions between hydroxy groups on adjacent aromatic rings. This locked conformation imparts a "bowl-shaped" structure to the all-cis calix[4]arene.

The molecular glass compounds include those having a high $T_g$ of 80° C. or greater, but which retain an amorphous character. Increasing $T_g$ to above 80° C. is accomplished by structural modification of the core calix[4]arenes (e.g., by inclusion of the sterically bulky aromatic aldehydes having a fused polycyclic aromatic or heteroaromatic structure) or by a combination of the structural modification to the core calix[4]arene and further structural changes to the side chains (as by including a sterically bulky or rigid pendant group and/or protecting group). These molecular glass compounds preferably have a $T_g$ above 100° C., and as high as 120° C. or more, while maintaining good film forming properties and amorphous character. Upon exposure of a coated film of photoresist prepared using the molecular glass compound and a photoacid generator, acid hydrolysis of the acetal protecting group renders the core soluble in alkaline developer.

Photoresists based on these molecular glass compounds provide good solubility contrast, and are also desirable since the increased $T_g$ of the molecular glass compounds imparts more robust lithographic processing conditions to the photoresist, e.g., in the post-apply bake (PAB), post-exposure bake (PEB), stability to the increased temperatures typically encountered during subsequent substrate etch, and in an improved pattern collapse margin due to the increased photoresist film modulus, particularly when developing 22 nm lines or smaller.

Thus, the molecular glass compound is based on calix[4]arene preferably having a high $T_g$, which is the tetrameric reaction product of an aromatic compound containing a hydroxy group and a fused polycyclic aromatic or heteroaromatic aldehyde.

Preferably, the aromatic compound is of formula (I):

$$C_6R^1{}_x(OR^2)_y \qquad (I)$$

wherein $R^1$ is H, F, $C_{1-20}$ alkyl, $C_{1-20}$ haloalkyl, $C_{6-20}$ aryl, $C_{6-20}$ haloaryl, $C_{7-20}$ aralkyl, or $C_{7-20}$ haloaralkyl, $R^2$ is H, $C_{1-20}$ alkyl, $C_{1-20}$ haloalkyl, x is 6-y and y is 2 or 3, at least one $OR^2$ group is a hydroxy group, and at least two $OR^2$ groups are meta to one another. As used herein, the prefix "halo-" means that the group includes any halogen or combination thereof (F, Cl, Br, I). A preferred halogen is fluorine.

Exemplary aromatic compounds of formula (I) include resorcinol, pyrogallol, 3-methoxyphenol, or 3-ethoxyphenol.

Also preferably, the polycyclic or fused polycyclic aromatic aldehyde is of formula (II):

$$Ar^1—CHO \qquad (II)$$

wherein $Ar^1$ is a substituted, halosubstituted or unsubstituted $C_{4-20}$ heterocyclic aromatic-containing moiety, or a substituted, halosubstituted or unsubstituted $C_{8-20}$ fused polycylic aromatic moiety. Preferably, $Ar^1$ of Formula (II) is a $C_{8-30}$ aryl, $C_{8-30}$ heteroaryl, $C_{8-30}$ haloaryl, $C_{8-30}$ heterohaloaryl, $C_{8-30}$ aralkyl, or $C_{7-20}$ haloaralkyl. As used herein, "substituted" means including a substituent such as a halogen (i.e., F, Cl, Br, I), hydroxy, amino, thiol, carboxyl, carboxylate, amide, nitrile, thiol, sulfide, disulfide, nitro, a $C_{1-10}$ alkyl, a $C_{1-10}$ alkoxy, a $C_{6-10}$ aryl, a $C_{6-10}$ aryloxy, a $C_{7-10}$ alkyl aryl, a $C_{7-10}$ alkyl aryloxy, or a combination comprising at least one of the foregoing. "Halosubstituted" means that the group specifically includes a halogen substituent (i.e., F, Cl, Br, I), and may include these halogens alone, or in combination with other substituents listed above. It will be understood that any group or structure disclosed with respect to the formulas herein may be so substituted unless otherwise specified, or where such substitution would significantly adversely affect the desired properties of the resulting structure.

More preferably, the polycyclic or fused polycyclic aromatic aldehyde of formula (II) includes an aldehyde of formula (III) or (IV):

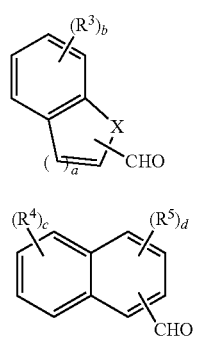

wherein X is $C(R^6)_2$, $NR^7$, S, or O, $R^3$ to $R^7$ are each independently H, F, $C_{1-20}$ alkyl, $C_{1-20}$ haloalkyl, $C_{6-20}$ aryl, $C_{6-20}$ haloaryl, $C_{7-20}$ aralkyl, or $C_{7-20}$ haloaralkyl, a, c, and d are each independently an integer of 1 to 3, and b is an integer of 1 to 4+a.

Exemplary fused-ring aromatic aldehydes include the following structures:

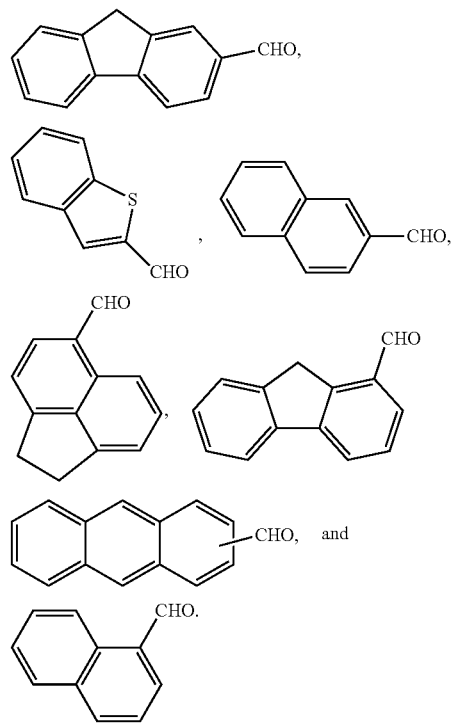

The calix[4]arene cores are thus formed as the reaction product of the condensation of compounds of formulas (I) and (II). Exemplary such calix[4]arenes include those having the following structures:

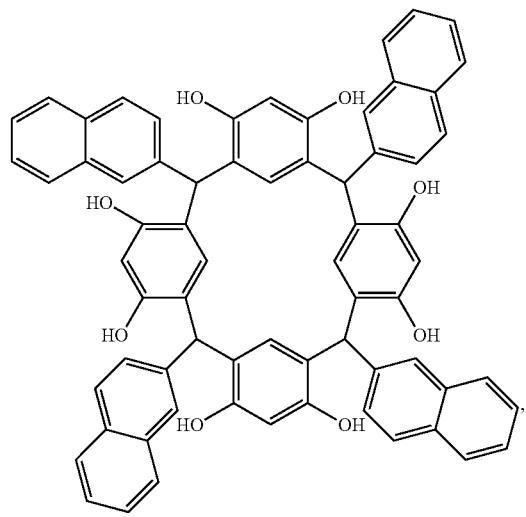

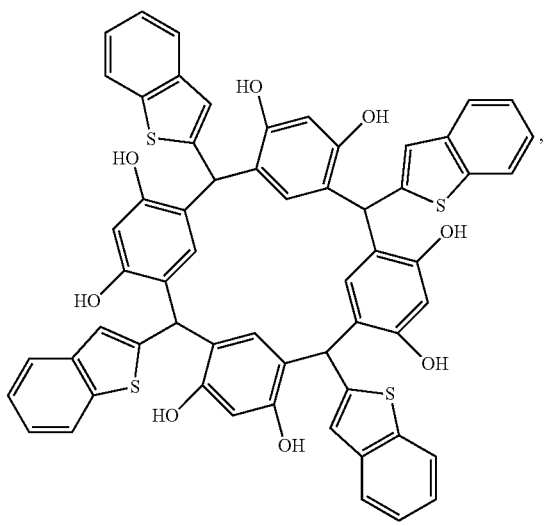

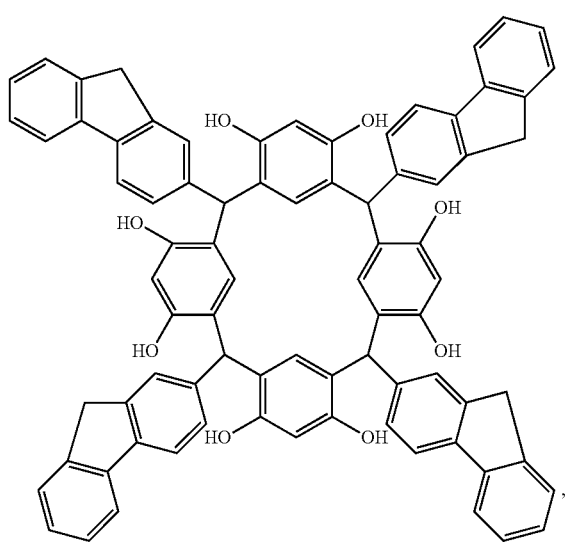

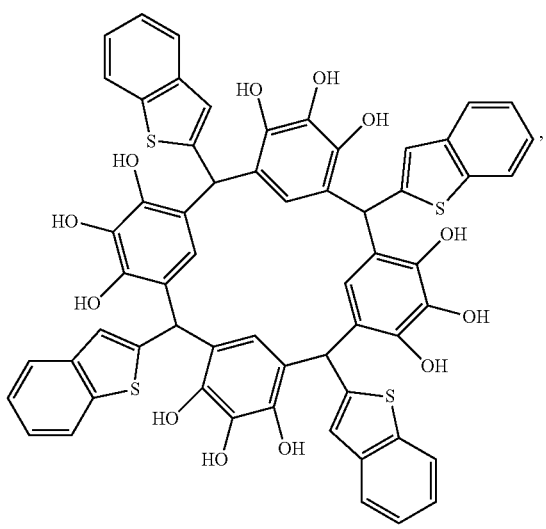

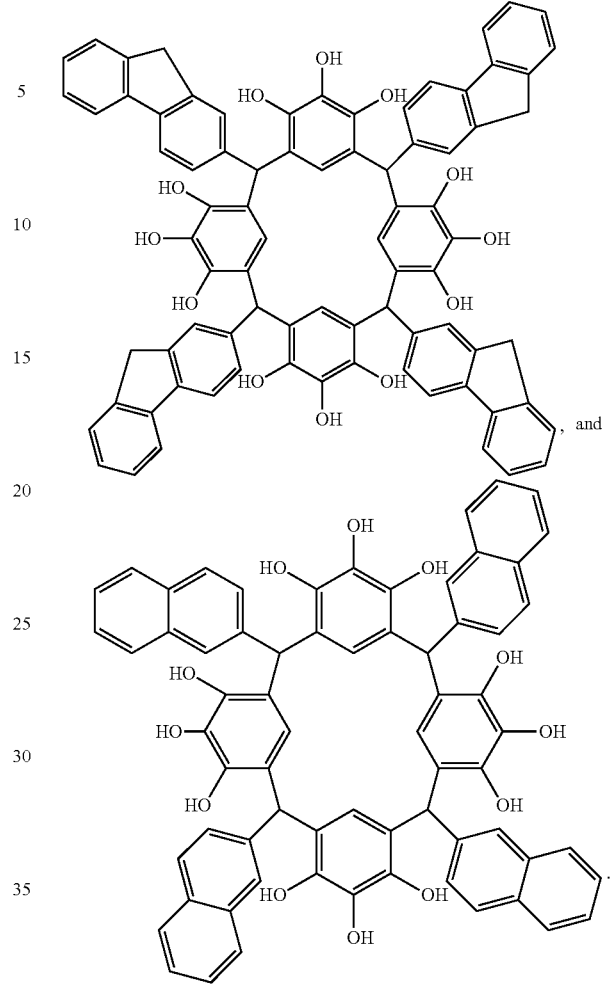

, and

The molecular glass compound further comprises an acid-removable protecting group as an adduct with the tetrameric reaction product calix[4]arene. The adduct is formed with the hydroxy group of the aromatic compound, a hydroxy group of the polycyclic or fused polycyclic aromatic aldehyde, or a combination comprising at least one of the foregoing. The acid-removable protecting group is preferably the adduct of a vinyl ether, a tertiary alkyl ester, a tertiary alkyl carbonyl, or a combination comprising at least one of the foregoing.

The acid removable group includes a moiety having a tertiary carbon center, as in the formula (V):

$$-(L^1)_m-C(=O)-O-C(R^8)_3 \qquad (V)$$

wherein $L^1$ is a $C_{1-20}$ linking group, m is 0 or 1, and each $R^8$ is independently substituted or unsubstituted and is a $C_{1-20}$ alkyl, $C_{1-20}$ haloalkyl, $C_{6-20}$ aryl, $C_{6-20}$ haloaryl, $C_{7-20}$ aralkyl, or $C_{7-20}$ haloaralkyl, wherein two or more adjacent $R^8$ groups are optionally connected to each other by a single bond. An exemplary such group $C(R^8)_3$ is a t-butyl group (i.e., formula (V) where $R^8$ is methyl). For example, where $R^8$ is methyl and m is 0, the acid removable group can be a t-butyloxycarbonyl (t-BOC) group, or where $R^8$ is methyl and m is 1, the acid removable group is a t-butyl acetate ester derived from a haloacetic acid t-butyl ester.

Alternatively, or in addition, the acid-removable protection group is preferably an adduct of a hydroxy group of the tetrameric reaction product and an aromatic vinyl ether of formula (VI):

$$C(R^9)_2=C(R^{10})-O-(L)_n-R^{11} \quad (VI)$$

wherein $R^9$ and $R^{10}$ are each independently a single bond, H, $C_{1-20}$ alkyl, $C_{1-20}$ haloalkyl, $C_{6-20}$ aryl, $C_{6-20}$ haloaryl, $C_{7-20}$ aralkyl, or $C_{7-20}$ haloaralkyl, L is a $C_{1-20}$ linking group, n is 0 or 1, and $R^{11}$ is a substituted or unsubstituted, monocyclic, polycyclic or fused polycyclic $C_{1-20}$ aliphatic group or $C_{6-20}$ aromatic-containing group, wherein $R^9$ and $R^{10}$ are connected to $R^{11}$ when either or both of $R^9$ and $R^{10}$ is a single bond and n is 0.

A combination comprising at least one of the foregoing acid removable groups may be used.

Exemplary aromatic vinyl ethers include those having the following formulas:

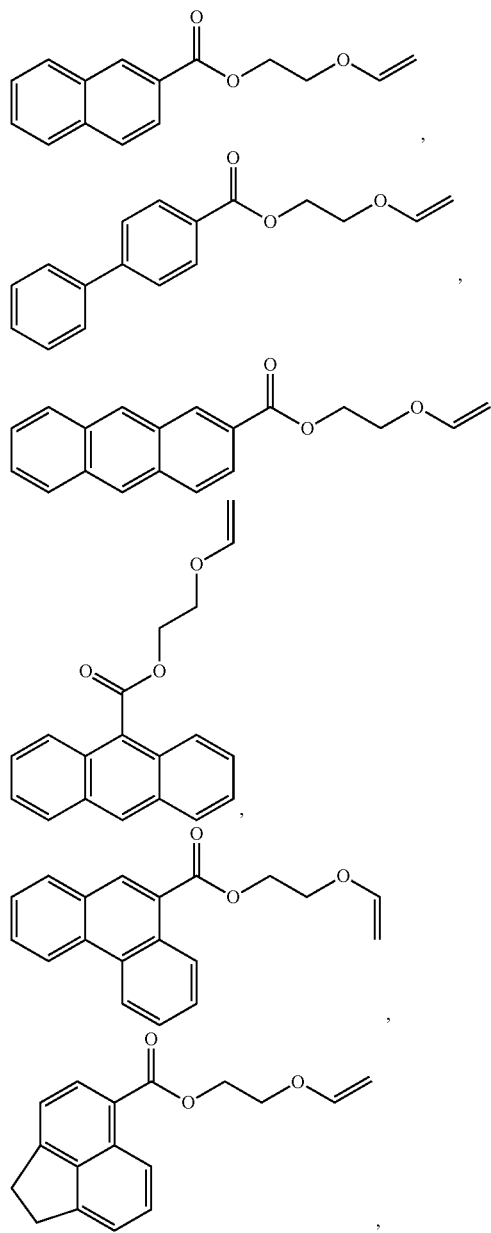

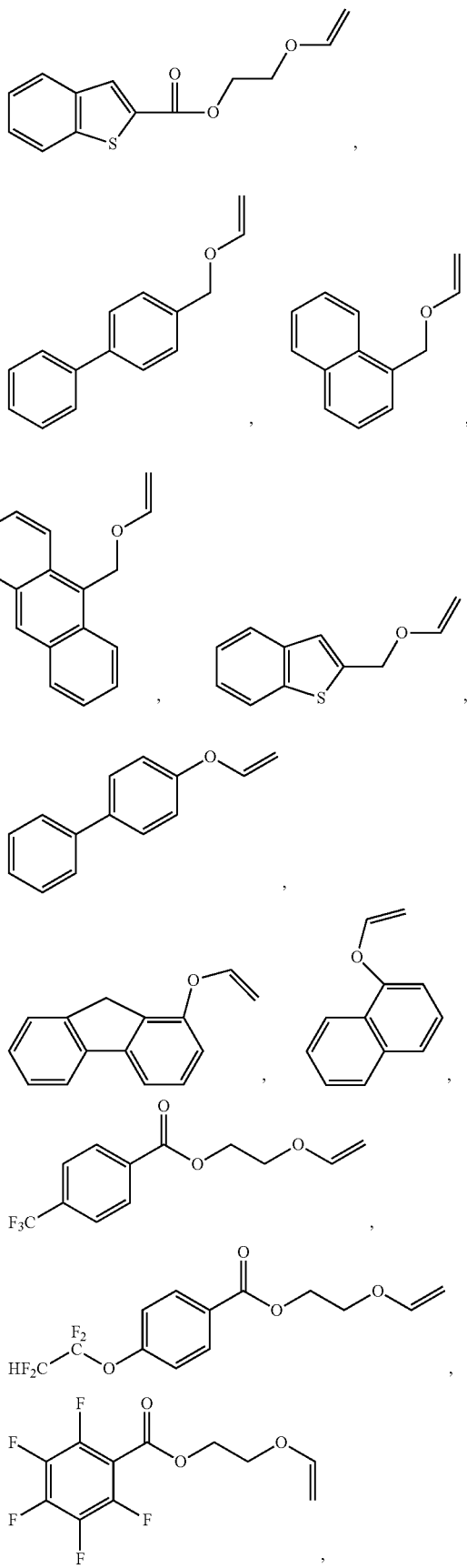

-continued

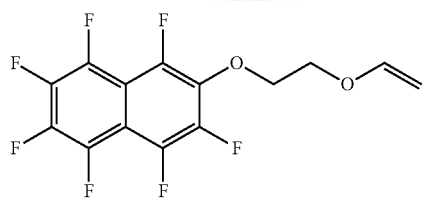,

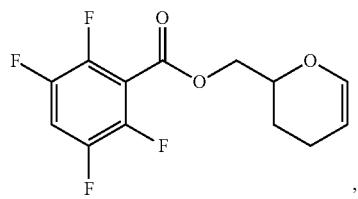,

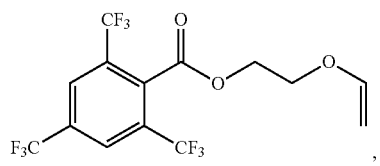,

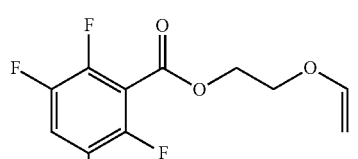,

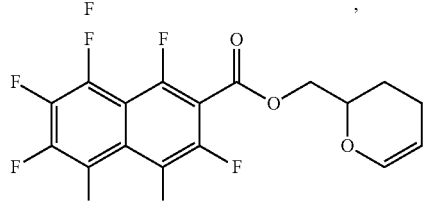,

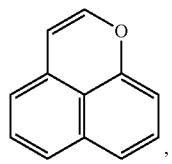,

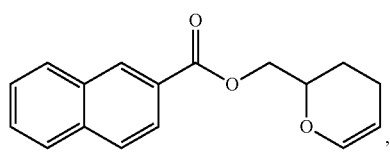,

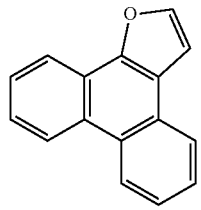,

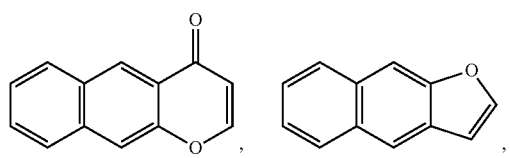,

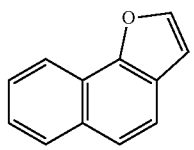, 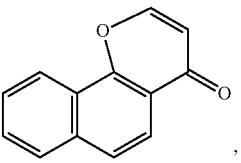, or a combination comprising at least one of the foregoing.

Exemplary cycloaliphatic vinyl ethers include those based on carbon cage structure such as internal or pendant cycloaliphatic or halosubstituted cycloaliphatic compounds:

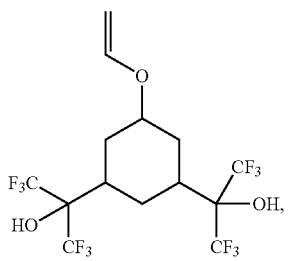,

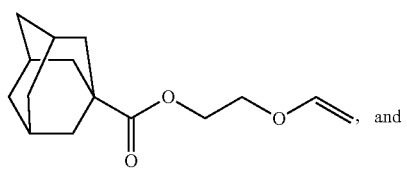, and

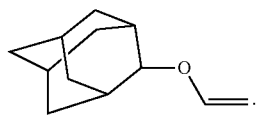.

Further exemplary aromatic vinyl ethers include those of general structure:

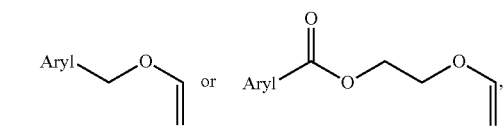, or a combination comprising at least one of the foregoing, wherein Aryl is, for example, an aromatic moiety having one of the following structures:

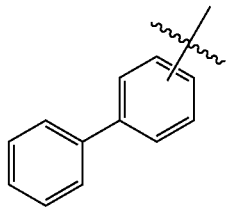,

-continued

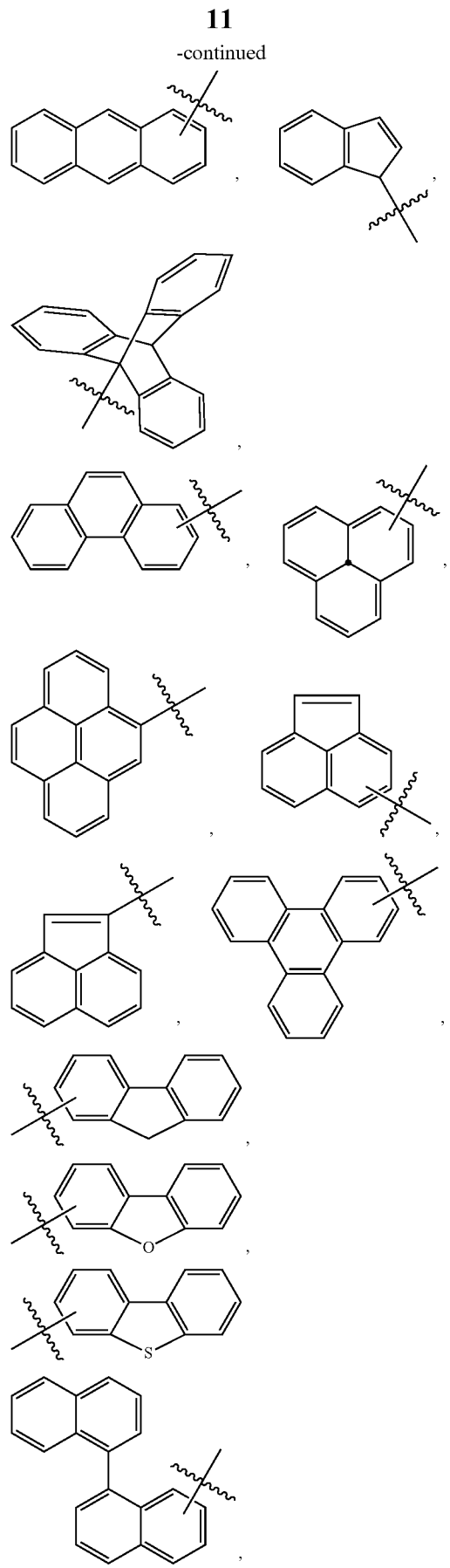

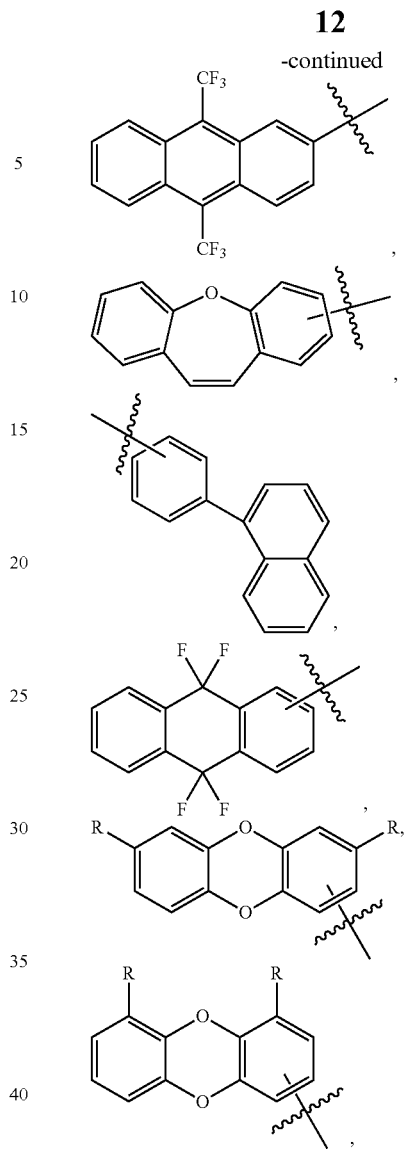

or a combination comprising at least one of the foregoing.

Alternatively, or in addition, the calix[4]arene can include protection groups that are non-acid removable. Preferably, such non-acid removable protection groups include non-tertiary (i.e., primary or secondary alcohol esters of) $C_{1-20}$ carboxylic acid or sulfonic acid esters, $C_{6-20}$ aryl carboxylic acid or sulfonic acid esters, and non-benzylic $C_{7-20}$ aralkyl carboxylic acid or sulfonic acid esters. Exemplary such groups include those derived from reactive derivatives of acetic acid, benzoic acid, halobenzoic acids, methanesulfonic acid, cyclohexanesulfonic acid, and perfluoroalkanesulfonic acids such as trifluoromethanesulfonic acid and perfluorobutanesulfonic acid.

The level of protection of any specific calix[4]arene core can vary based on the number of hydroxy groups located on the core. Protection chemistry leads to mixtures of molecular glass compounds with varying levels of protection which can, if desired, be separated by chromatography or other separation methods to isolate individual molecular glass compounds with same level of protection. Alternatively, or in addition, mixtures of molecular glass compounds having different levels of protection can be used directly in a photoresist. Where the core includes, for example, a resorcinol and a non-hydroxy-containing aldehyde, the number of sites covered by the protecting group for any given core can be 0 to 8, or where the core includes pyrogallol instead of resorcinol, the number of sites covered by the protecting group for a given core can be 0 to 12. The average level of protection for the molecular glass compound is 1 to 12, preferably 1 to 8, and more preferably 3 to 6.

Calixarene cores having at least 3 protecting groups, and as many as 8 protecting groups or more, are insoluble in alkaline developer (e.g. 0.26N aqueous tetramethylammonium hydroxide, abbreviated TMAH). The acetal linkage is acid cleavable by photogenerated acid, providing good solubility contrast under typical positive tone lithographic exposure/development processes.

Preferably, the molecular glass compound has a glass transition temperature of greater than or equal to 80° C., more preferably greater than or equal to 90° C., and most preferably greater than or equal to 100° C.

The calix[4]arene is the condensation reaction product of the above aromatic compound and aldehyde or derivative thereof, carried out in acidified polar solvent, such as aqueous acidic solution, an acidified alcohol-water mixture, or an acidified alcohol mixture. Suitable solvents and solvent mixtures for carrying out the condensation include, but are not limited to, hydrochloric acid in water, in methanol, ethanol, propanol, ethylene glycol, propylene glycol, ethylene glycol methyl ether, propylene glycol methyl ether, and combinations of the foregoing alcohols with water. Preferably, the solvent system is selected such that the cis-cis-cis isomer of the calix[4]arene precipitates preferentially. The condensation may be carried out at a temperature greater than about 70° C., more preferably greater than about 80° C. The calix[4]arene can be recovered as a precipitate, where the thermodynamic product (the cis-cis-cis isomer) can have lower solubility in aqueous solvents and can thus be isolated as a precipitate.

The condensation may be carried out in batch mode, by batch addition of monomers and acid catalyst to the reaction, by metered addition of separate feeds of one or more of the components (aromatic compound and aldehyde) to the reaction mixture, or any other suitable method for combining the reactants. As disclosed herein, the calix[4]arenes are discrete molecules and are not polymeric, and have a homogeneous composition, being the condensation product of a single aromatic compound with a single aldehyde; though it will be appreciated that while a polymeric intermediate (a condensation homopolymer) is initially formed, the calix[4]arene is the thermodynamic product of both oligomerization to directly obtain the calix[4]arene, and chain scission and end-group recombination of tetrameric segments of any intermediate polymer or thermodynamically disfavored conformer (i.e., cis-cis-trans, cis-trans-cis, trans-trans-trans).

The calix[4]arenes may have a molecular weight of less than or equal to 2,000 g/mol, preferably less than or equal to 1,500 g/mol. It will be appreciated that due to the nature of the condensed tetrameric product, the calix[4]arene core itself has a discrete and defined stoichiometry and hence has a theoretical polydispersity of 1. Molecular weights may be determined for the discrete compounds using mass spectrometry, such as for example field-desorption mass spectrometry, laser ablation mass spectrometry, or other methods suitable for obtaining the molecular weight of the calix[4]arene core and adducts.

The adduct is the further condensation product of the aromatic vinyl ether with the calix[4]arene.

The adduct of the calix[4]arene with the aromatic vinyl ether may be prepared by the reaction of the vinyl ether with the hydroxy group on the calix[4]arene in the presence of an acid catalyst to form the phenolic vinyl ether adduct. An exemplary solvent includes any suitable non-reactive solvent that can be used in a distillative drying process, including an aromatic compound, or an ether.

For example, the calix[4]arene from the condensation of resorcinol and 3-ethoxy-4-hydroxybenzaldehyde may be treated with a vinyl ether such as, for example, 2-(2-vinyloxy) ethyl naphthalene-2-carboxylate (NCVE), alone or in combination with 2-(2-vinyloxy)ethyl adamantanecarboxylate (AdCVE), in the presence of a catalytic amount of acid (e.g., trifluoroacetic acid) and low moisture content (<0.1% w/w) in a solvent including anisole, tetrahydrofuran, dioxane, 1,3-dioxolane, or 1-methoxy-2-propyl acetate. The aromatic vinyl ether adduct of the calix[4]arene (i.e., the molecular glass compound) may be used as a solution in a suitable solvent useful in preparing photoresist compositions, or may be isolated as a solid by precipitation or spray-drying.

A photoresist is prepared from the molecular glass compound. The photoresist includes, in addition to the molecular glass compound, a solvent, and a photoacid generator.

Solvents include those suitable for use in photoresists. Exemplary solvents include anisole, alcohols including, 1-methoxy-2-propanol, and 1-ethoxy-2 propanol, esters including ethyl lactate, n-butylacetate, 1-methoxy-2-propyl acetate, methoxyethoxypropionate, ethoxyethoxypropionate, ketones including cyclohexanone, methyl hydroxyisobutyrate and 2-heptanone, and a combination comprising at least one of the foregoing solvents.

Photoacid generators include generally those photoacid generators suitable for the purpose of preparing photoresists. Photoacid generators include, for example, an onium salt such as a mono- or diaryl iodonium or a mono-, di- or triaryl sulfonium salt, nitrobenzyl ester, sulfonic acid esters, diazomethane derivatives, glyoxime derivatives, sulfonic acid ester derivatives of an N-hydroxyimide compound and halogen-containing triazine compounds, or a combination comprising at least one of the foregoing, where the anion of the salt is a fluorinated or non fluorinated $C_{1-40}$ sulfonic acid or sulfonimide anion.

Other components that may be included in the photoresist include a photo-destroyable base, a quencher, and/or a surfactant.

Photo-destroyable bases include photo-decomposable cations, and preferably those useful for preparing PAGs, paired with an anion of a weak (pKa>2) acid such as, for example, a $C_{1-20}$ carboxylic acid. Exemplary such carboxylic acids include formic acid, acetic acid, propionic acid, tartaric acid, succinic acid, cyclohexylcarboxylic acid, benzoic acid, salicylic acid, and other such carboxylic acids. Exemplary photo-destroyable bases include those combining cations and anions of the following structures where the cation is triphenylsulfonium or one of the following:

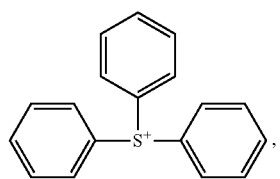

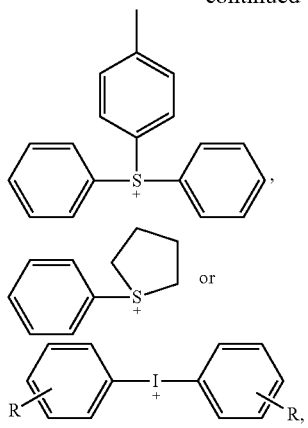

where R is independently H, a $C_{1-20}$ alkyl, a $C_{6-20}$ aryl, or a $C_{6-20}$ alkyl aryl, and the anion is

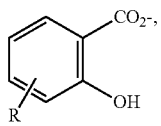

RC(=O)—O⁻, or ⁻OH,
where R is independently H, a $C_{1-20}$ alkyl, a $C_{1-20}$ alkoxy, a $C_{6-20}$ aryl, or a $C_{6-20}$ alkyl aryl. Other photo-destroyable bases include those based on non-ionic photo-decomposing chromophores such as, for example, 2-nitrobenzyl groups and benzoin groups.

Surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova.

Alternatively, or in addition, other additives may include quenchers that are non-photo-destroyable bases, such as, for example, those based on hydroxides, carboxylates, amines, imines, and amides. Preferably, such quenchers include $C_{1-30}$ organic amines, imines, or amides, or may be a $C_{1-30}$ quaternary ammonium salt of a strong base (e.g., a hydroxide or alkoxide) or a weak base (e.g., a carboxylate). Exemplary quenchers include amines such as Troger's base, a hindered amine such as diazabicyclo undecene (DBU) or diazabicyclononene (DBM), or ionic quenchers including quaternary alkyl ammonium salts such as tetrabutylammonium hydroxide (TBAH), tetramethylammonium 2-hydroxybenzoic acid (TMA OHBA), or tetrabutyl ammonium lactate. Other additives including dissolution rate inhibitors and sensitizers commonly used in the art may also be included in the photoresist.

The photoresist composition disclosed herein may include the molecular glass compound in an amount of 50 to 99 wt %, preferably 55 to 95 wt %, more preferably 60 to 90 wt %, and still more preferably 65 to 90 wt % based on the total weight of solids. It will be understood that "molecular glass compound" used in this context of a component in a photoresist may mean only the molecular glass compounds disclosed herein, or a combination of the molecular glass compound with another molecular glass compound or polymer useful in a photoresist. The photoacid generator may be included in an amount of 0.1 to 50 wt %, preferably 0.5 to 40 wt %, more preferably 1 to 20 wt %, and still more preferably 2 to 15 wt % based on the total weight of solids. Where used, the photo-destroyable base may be included at of 0.01 to 5 wt %, preferably 0.1 to 4 wt %, and still more preferably 0.2 to 3 wt %, based on the total weight of solids. A surfactant may be included in an amount of 0.01 to 5 wt %, preferably 0.1 to 4 wt %, and still more preferably 0.2 to 3 wt %, based on the total weight of solids. A quencher may be included in relatively small amounts of for example, from 0.03 to 5 wt % based on the total weight of solids. Other additives may be included in amounts of less than or equal to 30 wt %, preferably less than or equal to 20%, or more preferably less than or equal to 10%, based on the total weight of solids. The total solids content for the photoresist composition may be 0.01 to 50 wt %, preferably 0.1 to 40 wt %, more preferably 0.5 to 30 wt %, and still more preferably 1 to 20 wt %, based on the total weight of solids and solvent. It will be understood that the solids includes molecular glass and any associated polymer, photoacid generator, and any optional photo-destroyable base, quencher, surfactant, and additives, exclusive of solvent. It will be further understood that photoresist solids will be selected to provide the desired film thickness and so the total solids in solution is application-specific and should not be considered as limited to these solids contents.

The photoresist composition may be cast to form a layer on a substrate. Preferably, a photoresist layer thus comprises the molecular glass compound and photoacid generator after removal of solvent, and any additives such as photo-destroyable base and surfactant contacted to the surface of the substrate. Substrates may be any dimension and shape, and are preferably those useful for photolithography, such as silicon, silicon dioxide, strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. Preferably, the surfaces of substrates herein include critical dimension layers to be patterned including, for example, one or more gate-level layers or other critical dimension layer on the substrates for semiconductor manufacture. Such substrates may preferably include silicon, SOI, strained silicon, and other such substrate materials, formed as circular wafers having dimensions such as, for example, 20 cm, 30 cm, 40 cm, or larger in diameter, or other dimensions useful for wafer fabrication production.

Further, a method of forming an electronic device includes (a) applying a layer of a photoresist composition including the molecular glass compound on a surface of the substrate; and (b) patternwise exposing the photoresist composition layer to activating radiation. The method further include (c) developing the exposed photoresist composition layer to provide a resist relief image.

Applying may be accomplished by any suitable method, including spin coating, spray coating, dip coating, doctor blading, or the like. Applying the layer of photoresist is preferably accomplished by spin-coating the photoresist in solvent using a coating track, in which the photoresist is dispensed on a spinning wafer. During dispense, the wafer may be spun at a speed of up to 4,000 rpm, preferably from about 500 to 3,000 rpm, and more preferably 700 to 2,500 rpm. The coated wafer is spun to remove solvent, and is generally baked on a hot plate in a post-apply bake (PAB), also referred to in the art as a "soft bake," to further remove residual solvent and to remove free volume from the film to make it uniformly dense. Preferably, applying thus further includes a post-apply bake. A post-apply bake can be carried out at any suitable temperature. For example, a PAB can be carried out at less than or equal to about 120° C., preferably less than or equal to 110° C., and more preferably less than or equal to 100° C. A post-apply bake can be carried out for any suitable time, such as for example, less than or equal to about 120 seconds, preferably less than or equal to 110 seconds, and more preferably less than or equal to 100 seconds.

Patternwise exposure is then carried out using an exposure tool such as a stepper, in which the film is irradiated through a pattern mask and thereby is exposed patternwise. The method preferably uses advanced exposure tools generating activating radiation at wavelengths capable of high resolution. Thus, exposing is preferably carried out using e-beam radiation or extreme-ultraviolet (EUV) radiation. It will be appreciated that exposure using the activating radiation decomposes the PAG in the exposed areas and generates acid and decomposition by-products, and that the acid then effects a chemical change in the polymer (deblocking the acid sensitive group to generate a base-soluble group, or alternatively, catalyzing a cross-linking reaction in the exposed areas). The resolution of such exposure tools may be less than 30 nm.

After exposing, deblocking and/or catalyzing of a cross-linking reaction is further effected by performing a post-exposure bake (PEB), to diffuse the acid generated during exposing. A post-exposure bake can be carried out at any suitable temperature. For example, a PEB can be carried out at less than or equal to about 150° C., preferably less than or equal to 140° C., and more preferably less than or equal to 130° C. A post-exposure bake can be carried out for any suitable time, such as for example, less than or equal to about 120 seconds, preferably less than or equal to 110 seconds, and more preferably less than or equal to 100 seconds.

Developing the exposed photoresist layer is then accomplished by treating the exposed layer with a suitable developer capable of selectively removing the exposed portions of the film (where the photoresist is positive tone) or removing the unexposed portions of the film (where the photoresist is negative tone). Preferably, the photoresist is positive tone based on a polymer having acid sensitive (deprotectable) groups, and the developer is preferably a metal-ion free tetraalkylammonium hydroxide solution, such as, for example, aqueous 0.26 N tetramethylammonium hydroxide. The pattern is formed after developing.

The photoresist may be used to fabricate electronic and optoelectronic devices such as memory devices, processor chips (CPU's), graphics chips, and other such devices.

All compounds used herein are available commercially except where a procedure is provided below. Structural characterization was carried out by nuclear magnetic resonance (NMR) spectrometry on an INOVA 400 Spectrometer with OMNI-PROBE (operating at 400 or 500 MHz for proton, respectively), from Varian. Molecular weights for the molecular glasses were determined using a Waters e2695 LC/3100 Mass Detector, manufactured by Waters Associates, running a reversed phase liquid chromatograph having a $C_{18}$ column, gradient elution with an acetonitrile/water, 80/20 to 100/0 (v/v) gradient at a flow of 0.5 mL/min with a high resolution mass spectrometer detector (LC-MS) to provide m/z. Glass transition temperature (Tg) was determined using a DSC Q2000 Differential Scanning calorimeter, manufactured by TA Instrument Inc., operating at a ramp rate of 10° C./min Unless otherwise specified, all reagents were obtained commercially.

Exemplary calix[4]arene cores were synthesized to contain different numbers of free hydroxy groups. The procedures are provided hereinbelow.

Calixarene Examples 1-5, 8, and 9 were each prepared according to the following general procedure. A phenolic compound (100 mmol) was added to 120 mL ethanol followed by addition of conc. HCL (10 mL), and the mixture was stirred at room temperature for 5 minutes. The desired aldehyde (100 mmol) was added dropwise to the mixture, followed by refluxing for 4-6 hours. The resulting mixture was cooled to room temperature, and the resulting solid was collected by filtration. The crude product was washed with water and methanol (3×50 mL), and dried in vacuo at 60° C. overnight.

Calixarene 6 (benzothiophene-resorcinol calix[4]arene) was prepared by the following method. To a 250 mL round bottom flask, resorcinol (2.00 g, 18.2 mmol), benzo[b]thiophene-2-carboxaldehyde (2.95 g, 18.2 mmol), ethanol (100 mL), and HCl (concentrated, 10 mL) were added. A nitrogen inlet was equipped and the reaction was stirred at 80° C. for 16 h. The reaction began as a clear solution but slowly formed a purple precipitate. After completion of the reaction, the resulting solution was filtered through a fritted funnel and the solid collected was washed with water (50 mL) and ethanol (50 mL). The washed product was dried in vacuo at 60° C. for 16 hours (yield: 4.05 g, 88%). LC-MS m/z=1017.2 g/mol.

Calixarene 7 (benzothiophene-pyrogallol calix[4]arene) was prepared by the following method. To a 250 mL round bottom flask, pyrogallol (1,2,3-trihydroxybenzene, 3.89 g, 30.8 mmol), benzo[b]thiophene-2-carboxaldehyde (5.00 g, 30.8 mmol), ethanol (100 mL), and HCl (concentrated, 10 mL) were added. A nitrogen inlet was equipped and the reaction was stirred at 80° C. for 16 hours. The reaction began as a clear solution but slowly formed a purple precipitate. After completion of the reaction, the resulting solution was filtered through a fritted funnel and the solid was washed with water (50 mL) and ethanol (50 mL). The product was dried in vacuo at 60° C. for 16 hours (yield: 6.30 g, 76%). LC-MS m/z=1081.2 g/mol.

The structures of the calixarenes of Examples 1-9 are shown below:

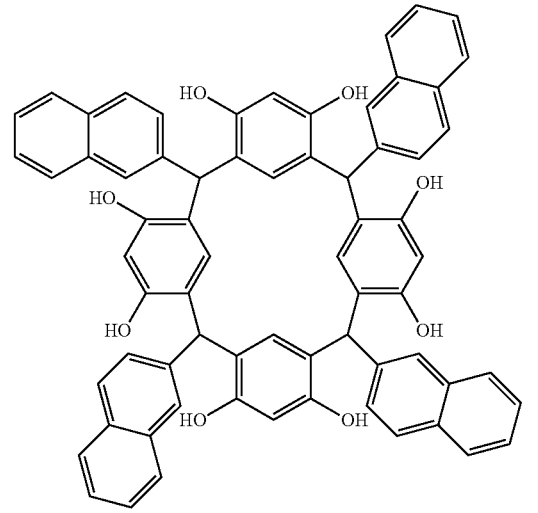

Example 1

Example 2
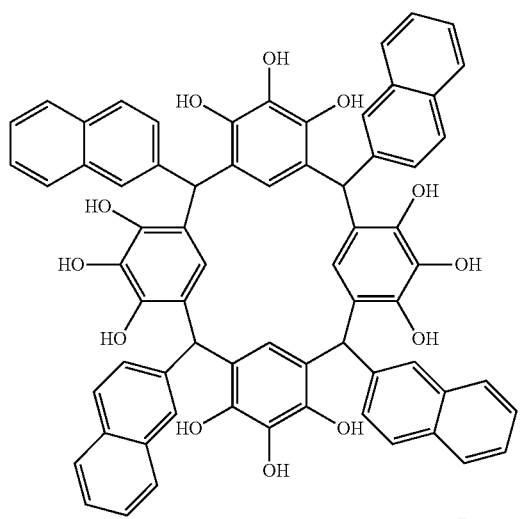
Example 3
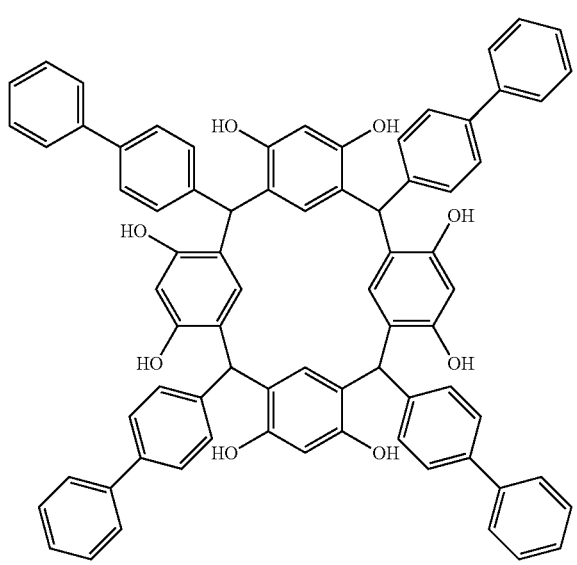
Example 4
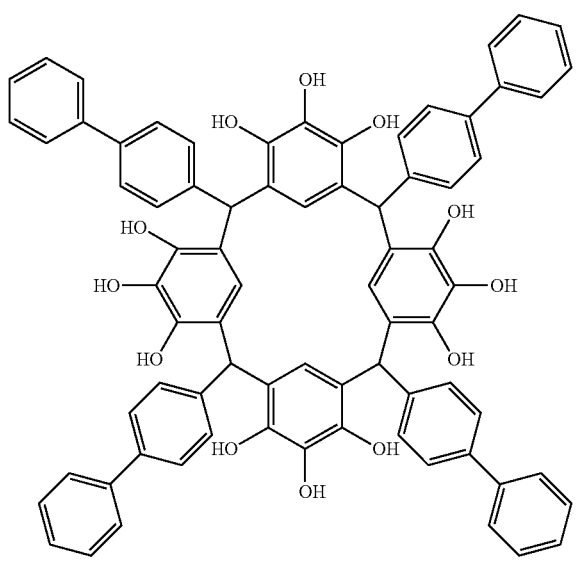
Example 5
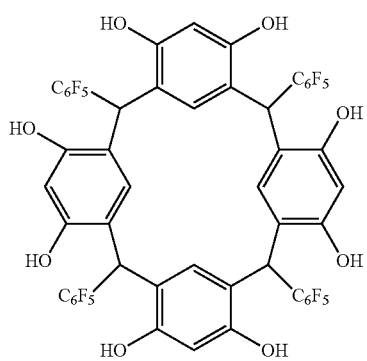
Example 6
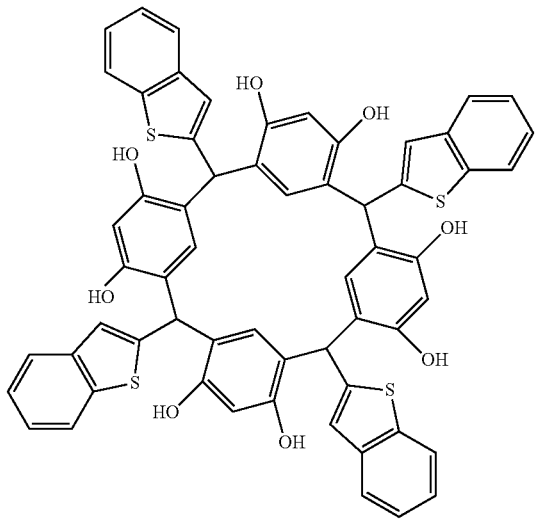
Example 7
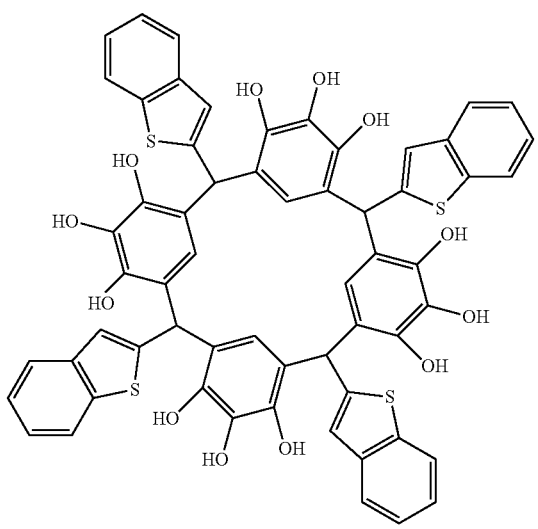

Example 8

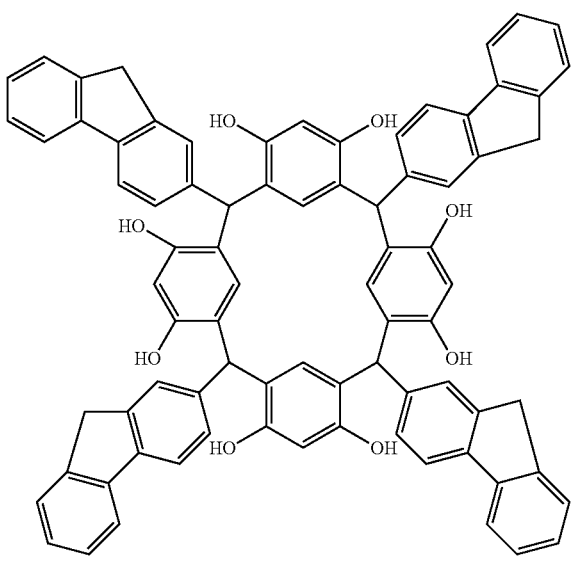

Example 9

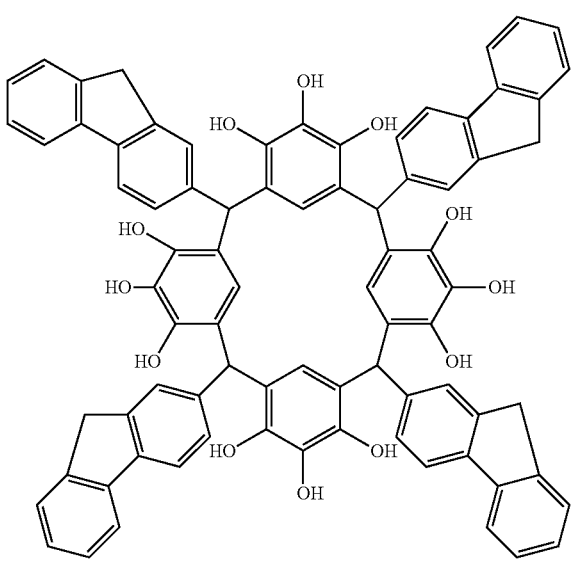

Physical data for the calixarenes of Examples 1-9 are shown in Table 1, below.

TABLE 1

| Example | Phenolic compound | Aldehyde | Yield (%) | MZ m/s |
|---|---|---|---|---|
| 1 | Resorcinol | 2-naphthaldehyde | 87 | 993.1 |
| 2 | Pyrogallol | 2-naphthaldehyde | 82 | 1057.1 |
| 3 | Resorcinol | 4-phenyl-benzaldehyde | 84 | 1097.25 |
| 4 | Pyrogallol | 4-phenyl-benzaldehyde | 91 | 1161.25 |
| 5 | Resorcinol | 2,3,4,5,6-penta-fluorobenzaldehyde | 44 | 1152.7 |
| 6 | Resorcinol | Benzothiophene-2-carboxaldehyde | 81 | 1017.21 |
| 7 | Pyrogallol | Benzothiophene-2-carboxaldehyde | 88 | 1081.21 |
| 8 | Resorcinol | Fluorene-2-Carboxaldehyde | 76 | 1145.3 |
| 9 | Pyrogallol | Fluorene-2-Carboxaldehyde | 88 | 1209.29 |

Vinyl ether adducts of calixarene Examples 1 to 9 were prepared from the following vinyl ether compounds:

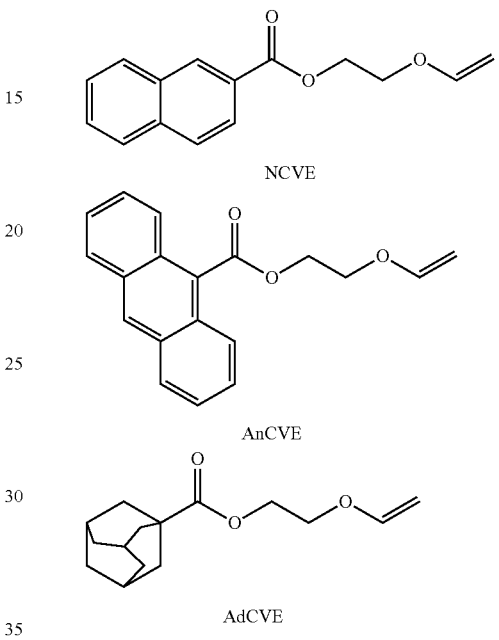

Procedures for preparing the vinyl ether compounds NCVE, AnCVE, and AdCVE are provided below.

2-Naphthyl carboxylic acid—2-ethyl vinyl ether (NCVE) was prepared as follows. In a 300 mL three necked oven dried round bottom flask equipped with a magnetic stirrer, 2-naphthoic acid (25 g, 0.145 mol) and potassium carbonate (24.0, 0.170 mol) were suspended in 100 ml of dioxane and the mixture stirred at room temperature for 1 hour, to form a thick slurry. 2-Chloroethylvinyl ether (18.5 g, 0.170 mol) was dissolved in 10 ml of dioxane and slowly added dropwise to the reaction mixture over a period of 1 hour. The reaction was further heated at reflux for an additional 12 hours until a complete reaction was ascertained by thin layer chromatography (TLC) analysis (silica plates; eluant 1% (v/v) methanol in chloroform). The reaction was quenched by pouring the mixture slowly into 400 ml of 0.01% (v/v) hydrochloric acid (HCl) solution and the crude product was extracted into 300 ml of ethyl acetate. The ethyl acetate extract was washed sequentially with water and brine to neutral pH and the ethyl acetate extracts were then dried over sodium sulfate, filtered and concentrated by rotary evaporation to afford the product as an amber oil (32.0 g, 92% yield) which solidifies upon standing. The product was used without further purification. $^1$H NMR (500 MHz, Acetone-$d_6$): δ 8.64 (s, 1H), 8.08 (d, 2H, 8 Hz), 7.89 (d, 2H, 8.5 Hz), 7.64-7.59 (q, 2H), 6.56-6.52 (d/d, 1H, 7 Hz), 5.58 (s, 1H), 4.60 (m, 2H), 4.49 (m, 2H), 2.30 (s, 3H), 1.90 (s, 3H). $^{13}$C NMR (125 MHz, CDCl$_3$): δ 166.6, 151.5, 135.6, 132.4, 131.3, 129.4, 128.3, 128.1, 127.7, 127.0, 126.6, 125.2, 87.1, 65.9, 63.3.

9-Anthracene carboxylic acid—2-ethyl vinyl ether (AnCVE) and 1-adamantanecarboxylic acid—2-ethyl vinyl ether (AdCVE) were each prepared according to the procedure detailed for NCVE above, with corresponding adjustments for the molecular weights of the anthracene carboxylic acid chloride and the adamantane carboxylic acid chloride, respectively.

Adducts of the above calix[4]arenes, protected with a vinyl ether compound (i.e., NCVE, AnCVE, or AdCVE) to form molecular glass compounds, were carried out according to the following general procedure as follows.

In a 500 mL round bottom flask was added the benzothiophene-resorcinol calix[4]arene core of Example 1-9 (10 mmol) and a vinyl ether (20-60 mmol of NCVE, AnCVE, or AdCVE). The flask was purged with nitrogen and anhydrous dioxane (150 mL) was added. To the heterogeneous solution was added trifluoroacetic acid (about 10 drops) and the reaction was heated to 60° C. for 16 hours. After 3 hours, the solution changed from a heterogeneous solution to a clear dark solution. At the completion of the reaction the solution was allowed to cool to room temperature and triethylamine (20 drops) was added. All volatiles were removed via rotary evaporator and the viscous oil was triturated with hexanes until a precipitate formed. The heterogeneous solution was filtered through a fritted funnel and the solid was collected. Acetonitrile was added to the solids to prepare a solution having 50 wt % solids, and reverse phase column chromatography was performed to separate each of the components. The product was dried in vacuo at 50° C. for 16 hours (yield: 85-95% based on the combined moles of any isolated components or the blend) and differential scanning calorimetry (DSC) analysis was performed to determine the glass transition temperature ($T_g$). The $T_g$ data for each adduct is provided in Table 2, below. Where a blend is indicated, an equimolar mixture of n=4, n=5, and n=6 adducts are used.

TABLE 2

| Example | Example 6 - (vinyl ether)$_n$ | Vinyl Ether | $T_g$ (in ° C.) |
|---|---|---|---|
| 10 | n = 2 | AnCVE | 114.8 |
| 11 | n = 3 | NCVE | 115.3 |
| 12 | n = 3 | AnCVE | 121.6 |
| 13 | n = 4 | NCVE | 100 |
| 14 | n = 4 | AnCVE | 107.9 |
| 15 | n = 5 | AnCVE | 99.8 |
| 16 | n = 4, 5, 6 blend | AdCVE | 86.6 |

The NCVE adducts were formulated into photoresist compositions and evaluated lithographically.

An additional polymer for lithographic analysis (Comparative Polymer 1) was prepared as follows. Commercially available polyhydroxystyrene/styrene p(HS/Sty) (30 g, 90/10 HS/Sty ratio, Mw=5,444, Mw/Mn 1.28, obtained from Toyo Gosei Co.) was dissolved in 100 g of 1,3-dioxolane. About 50 g of the dioxolane was distilled off under reduced pressure to azeotropically remove residual water from the polymer solution. The solution was cooled and 3.8 g (0.016 mol) of 2-naphthoylethylvinylether and 0.28 g of trifluoroacetic acid (TFA) were added. The mixture was stirred for 8 hours at room temperature. Upon completion (as determined by gas chromatography), residual acid was neutralized by adding 0.24 g (2.5 mmol) of triethylamine. The resultant polymer was obtained by diluting the reaction mixture to 15% solids in dioxane and precipitating the polymer by addition to an excess volume of heptanes, to afford the NCVE adduct of the polymer in a compositional ratio of 63/10/27 of p(HS/Sty/NCVE), respectively, as determined by $^{13}C$ NMR, in quantitative yield. Weight averaged molecular weight (Mw) was determined to be 5,700 g/mol with a polydispersity (Mw/Mn) of 1.3 by GPC using universal calibration to polystyrene standards.

The comparative and exemplary photoresist compositions were formulated as follows.

A positive tone photoresist composition (Comparative Photoresist 1) was prepared using the following procedure. Commercially available polymer HSIIA2 (0.215 g; available from Idemitsu), 0.053 g of a 1 wt % solution of POLYFOX PF656 surfactant in propylene glycol monomethyl ether acetate, 0.215 g of a 1 wt % solution of base additive (tetramethylammonium o-hydroxybenzoate; TMA-OHBA) in ethyl lactate, 0.646 g of a 5 wt % solution of triphenylphenylsulfonium cyclo-(1,3-perflouropropanedisulfonyl)imide salt in propylene glycol monomethyl ether acetate, 5.94 g of ethyl lactate and 2.92 g of hydroxy methyl isobutyrate (HBM) were thoroughly mixed to dissolve the solids and filtered through a 0.1 μm filter.

A positive tone photoresist composition (Comparative Photoresist 2) was prepared using the following procedure. A positive tone photoresist composition was prepared by combining in a mixture of 0.108 g of Comparative Polymer 1 (PHS/HS/NCVE), 0.022 g of a 1 wt % solution of POLYFOX PF656 surfactant in propylene glycol monomethyl ether acetate, 0.108 g of a 1 wt % solution of base additive (TMA-OHBA) in ethyl lactate, 0.323 g of a 5 wt % solution of triphenylsulfonium cyclo-(1,3-perflouropropanedisulfonyl)imide salt in propylene glycol monomethyl ether acetate solvent, 2.98 g of ethyl lactate and 1.46 g of hydroxy methyl isobutyrate (HBM) were thoroughly mixed to dissolve the solids and filtered through a 0.1 μm filter.

A positive tone photoresist composition (Photoresist 1) was prepared according to the following procedure. A mixture of 0.054 g of the NCVE protected calix[4]arene of Example 7 (n=4, 5, 6), 0.011 g of a 1 wt % solution of POLYFOX PF656 surfactant in propylene glycol monomethyl ether acetate, 0.054 of a 1 wt % solution of base additive (TMA-OHBA) in ethyl lactate, 0.161 g of a 5 wt % solution of triphenylsulfonium cyclo(1,3-perflouropropanedisulfonyl)imide salt in propylene glycol monomethyl ether acetate, 1.489 of ethyl lactate and 0.731 g of hydroxy methyl isobutyrate (HBM) were thoroughly mixed to dissolve the solids and filtered through a 0.1 μm filter.

A positive tone photoresist composition (Photoresist 2) was prepared according to the following procedure. A mixture of 0.215 g of NCVE protected example 4 (n=4), 0.053 g of a 1 wt % solution of POLYFOX PF656 surfactant in propylene glycol monomethyl ether acetate, 0.215 g of a 1 wt % solution of base additive (TMA-OHBA) in ethyl lactate, 0.646 g of a 5 wt % solution of triphenylsulfonium cyclo(1,3-perflouropropanedisulfonyl)imide salt in propylene glycol monomethyl ether acetate, 5.94 g of ethyl lactate and 2.92 g of hydroxy methyl isobutyrate (HBM) were thoroughly mixed to dissolve the solids and filtered through a 0.1 μm filter.

A positive tone photoresist composition (Photoresist 3) was prepared using the following procedure. A mixture of 0.215 g of NCVE protected calixarene of Example 6 (n=4), 0.053 g of a 1 wt % solution of POLYFOX PF656 surfactant in propylene glycol monomethyl ether acetate, 0.215 g of a 1 wt % solution of base additive (TMA-OHBA) in ethyl lactate, 0.646 g of a 5 wt % solution of triphenylsulfonium cyclo(1,3-perflouropropanedisulfonyl)imide salt in propylene glycol monomethyl ether acetate, 5.94 g of ethyl lactate and 2.92 g of hydroxy methyl isobutyrate (HBM) were thoroughly mixed to dissolve the solids and filtered (0.1 μm filtration).

Each comparative and exemplary photoresist was lithographically processed as follows. The photoresist was spin-coated using a TEL ACT-8 coating track (Tokyo Electron) onto a 200 mm silicon wafer with a commercially available organic underlayer (AR9, available from Dow Electronic Materials) and post-apply baked at 90° C. for 60 seconds to form a photoresist film of about 60 nm in thickness. The resulting photoresist layer was flood exposed using an $E_0$ array using an EUV-ES 9000 LTJ tool (EUV radiation, 13.4 nm). The patterned wafers were post exposure baked at 70-90° C. (see Table 3, below) and the image pattern developed with 0.26 N aqueous tetramethylammonium hydroxide developer solution to form a positive-tone photoresist pattern. The $E_0$ data is shown in Table 3, below.

TABLE 3

| Photoresist Example | Core | NCVE Adduct | AnCVE adduct | Tg (° C.) | PEB KrF temp/time | KrF $E_0$ mJ/cm² | PEB EUV temp/time | EUV $E_0$ mJ/cm² |
|---|---|---|---|---|---|---|---|---|
| Comparative Photoresist 1 | Commercial material | — | — | N/A | 90° c./60 s | 9.0 | 90° c./60 s | 5.5 |
| Comparative Photoresist 2 | PHS/HS | 27% NCVE | — | | 90° c./60 s | 20.0 | 90° c./60 s | 10.0 |
| Photoresist 1 | Example 7 | n = 4, 5, 6 | — | 82 | 70° c./60 s | 7.2 | 70° c./60 s | 5.5 |
| Photoresist 2 | Example 4 | n = 4 | — | 92 | 70° c./60 s | 5.8 | 70° c./60 s | 5.0 |
| Photoresist 3 | Example 6 | n = 4 | — | 100 | 80° c./60 s | 10.2 | 80° c./60 s | 8.0 |

As seen in Table 3, the photoresist adducts of Photoresists 1-3 each showed at least comparable $E_0$ behavior to the commercially available core. Photoresist 2, prepared using the core of Example 4, exhibited an $E_0$ at EUV wavelengths of 0.5 mJ/cm² less than that of the fastest comparative photoresist (Comparative Photoresist 1), and a significantly faster $E_0$ at DUV wavelengths (3.2 mJ/cm² faster).

All ranges disclosed herein are inclusive of the endpoints, and the endpoints are independently combinable with each other. The suffix "(s)" as used herein is intended to include both the singular and the plural of the term that it modifies, thereby including at least one of that term. "Optional" or "optionally" means that the subsequently described event or circumstance can or cannot occur, and that the description includes instances where the event occurs and instances where it does not. As used herein, "combination" is inclusive of blends, mixtures, alloys, or reaction products. All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. Further, it should further be noted that the terms "first," "second," and the like herein do not denote any order, quantity, or importance, but rather are used to distinguish one element from another.

The invention claimed is:

1. A molecular glass compound comprising:
   A.) a tetrameric reaction product of:
      an aromatic compound of formula (I):

$$C_6R^1{}_x(OR^2)_y \quad (I)$$

wherein $R^1$ is H, F, $C_{1-20}$ alkyl, $C_{1-20}$ haloalkyl, $C_{6-20}$ aryl, $C_{6-20}$ haloaryl, $C_{7-20}$ aralkyl, or $C_{7-20}$ haloaralkyl, $R^2$ is H, $C_{1-20}$ alkyl, $C_{1-20}$ haloalkyl, x is 6-y and y is 2 or 3, at least one $OR^2$ group is a hydroxy group, and at least two $OR^2$ groups are meta to one another, and a polycyclic or fused polycyclic aromatic aldehyde of formula (II)

$$Ar^1\text{—CHO} \quad (II)$$

wherein $Ar^1$ is a substituted, halosubstituted or unsubstituted $C_{4-20}$ heterocyclic aromatic-containing moiety, or a substituted, halosubstituted or unsubstituted $C_{8-20}$ fused polycylic aromatic moiety, and B.) an acid-removable protecting group as an adduct with the hydroxy group of the aromatic compound, a hydroxy group of the polycyclic or fused polycyclic aromatic aldehyde, or a combination comprising at least one of the foregoing; wherein the acid-removable protecting group is the adduct of an aromatic vinyl ether represented by formula (VI)

$$C(R^9)_2\text{=}C(R^{10})\text{—O-(L)}_n\text{-}R^{11} \quad (VI)$$

wherein $R^9$ and $R^{10}$ are each independently a single bond, H, $C_{1-20}$ alkyl, $C_{1-20}$ haloalkyl, $C_{6-20}$ aryl, $C_{6-20}$ haloaryl, $C_{7-20}$ aralkyl, or $C_{7-20}$ haloaralkyl, L is a $C_{1-20}$ linking group, n is 0 or 1, and $R^{11}$ is a substituted or unsubstituted, monocyclic, polycyclic or fused polycyclic $C_{1-20}$ aliphatic group or $C_{6-20}$ aromatic-containing group, wherein $R^9$ and $R^{10}$ are connected to $R^{11}$ when either or both of $R^9$ and $R^{10}$ is a single bond and n is 0.

2. The molecular glass compound of claim 1, wherein the aromatic compound of formula (I) is resorcinol, pyrogallol, 3-methoxyphenol, or 3-ethoxyphenol.

3. The molecular glass compound of claim 1, wherein $Ar^1$ of Formula (II) is a $C_{8-30}$ aryl, $C_{8-30}$ heteroaryl, $C_{8-30}$ haloaryl, $C_{8-30}$ heterohaloaryl, $C_{8-30}$ aralkyl, or $C_{7-20}$ haloaralkyl.

4. The molecular glass compound of claim 1, wherein the polycyclic or fused polycyclic aromatic aldehyde is of formulas (III) or (IV):

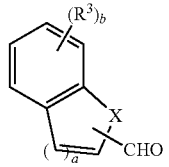

(III)

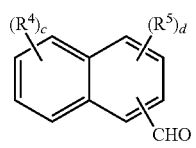

(IV)

wherein X is $C(R^6)_2$, $NR^7$, S, or O, $R^3$ to $R^7$ are each independently H, F, $C_{1-20}$ alkyl, $C_{1-20}$ haloalkyl, $C_{6-20}$ aryl, $C_{6-20}$ haloaryl, $C_{7-20}$ aralkyl, or $C_{7-20}$ haloaralkyl, a, c, and d are each independently an integer of 1 to 3, and b is an integer of 1 to 4+a.

5. A photoresist, comprising the molecular glass compound of claim 1.

6. A photoresist, comprising the molecular glass compound of claim 1, a solvent, and a photoacid generator.

7. A coated substrate, comprising: (a) a substrate having one or more layers to be patterned on a surface thereof; and (b) a layer of a photoresist composition of claim 6 over the one or more layers to be patterned.

8. A method of forming a patterned substrate, comprising exposing the coated substrate of claim 7 to activating radiation.

9. The method of claim 8, wherein exposure is with e-beam and/or EUV radiation.

* * * * *